(12) United States Patent
Chen et al.

(10) Patent No.: US 8,319,823 B2
(45) Date of Patent: Nov. 27, 2012

(54) SYSTEM AND METHOD FOR PANORAMIC IMAGE STITCHING

(75) Inventors: Mo Chen, Liverpool, NY (US); Daniel Francis Godici, Brewerton, NY (US)

(73) Assignee: JADAK, LLC, North Syracuse, NY (US)

( * ) Notice: Subject to any disclaimer, the term of this patent is extended or adjusted under 35 U.S.C. 154(b) by 546 days.

(21) Appl. No.: 12/611,460

(22) Filed: Nov. 3, 2009

(65) Prior Publication Data

US 2011/0102542 A1 May 5, 2011

(51) Int. Cl.
*H04N 7/00* (2006.01)
*G06K 9/00* (2006.01)

(52) U.S. Cl. ............... 348/37; 348/36; 382/190

(58) Field of Classification Search ............... 348/36–39; 382/100, 128, 190, 307; 73/290 R–334
See application file for complete search history.

(56) References Cited

U.S. PATENT DOCUMENTS

| | | | | |
|---|---|---|---|---|
| 3,966,332 A * | 6/1976 | Knapp et al. | ................... | 356/427 |
| 6,356,272 B1 * | 3/2002 | Matsumoto et al. | .......... | 345/582 |
| 7,545,972 B2 * | 6/2009 | Itoh | ................. | 382/142 |
| 7,982,201 B2 * | 7/2011 | Bryant et al. | ................. | 250/577 |
| 8,170,271 B2 * | 5/2012 | Chen | ............................ | 382/100 |
| 2002/0174437 A1 * | 11/2002 | Mano et al. | ..................... | 725/95 |
| 2003/0234866 A1 * | 12/2003 | Cutler | ........................ | 348/207.1 |
| 2005/0044179 A1 * | 2/2005 | Hunter | .......................... | 709/218 |
| 2008/0088836 A1 * | 4/2008 | Senn et al. | .................... | 356/256 |
| 2008/0267504 A1 * | 10/2008 | Schloter et al. | .............. | 382/181 |
| 2009/0041449 A1 * | 2/2009 | Kim | ................................ | 396/324 |
| 2009/0107234 A1 * | 4/2009 | Kim et al. | ....................... | 73/293 |
| 2009/0160930 A1 * | 6/2009 | Ruppert | ......................... | 348/37 |
| 2009/0324032 A1 * | 12/2009 | Chen | ............................ | 382/128 |
| 2011/0106312 A1 * | 5/2011 | Chen et al. | .................... | 700/259 |

* cited by examiner

*Primary Examiner* — Brendan Higa

(74) *Attorney, Agent, or Firm* — David L. Nocilly; Bond Schoeneck & King

(57) ABSTRACT

A system for capturing images of a target, such as a test tube, that is presented in front of an optical imager and rotated 360 degrees. The imager of the system captures a series of images which are then stitched together to form a panoramic image of the target. The panoramic image may then be processed to decode any barcode code information placed on the target, capture other information placed on the target, or obtain information about the target or the contents thereof.

13 Claims, 8 Drawing Sheets

SYSTEM AND METHOD FOR PANORAMIC IMAGE STITCHING

BACKGROUND OF THE INVENTION

1. Field of the Invention

The present invention relates to autoidentification systems and, more specifically, to a system and method for preparing panoramic optical images for autoidentification decoding processes.

2. Description of the Related Art

Machine vision plays an important role in automated and robotic systems, such as assembly line manufacturing, quality control inspection, and sample processing. Conventional systems are generally comprised of an optical imager, such as a charged coupled device (CCD) or similar device using digital imaging technology, which is positioned to capture images of objects that pass in front of it. In low-light or enclosed applications, machine vision systems may include an illumination source, such as a bank of light emitting diodes (LEDs), positioned proximately to the imager. The images are subsequently processed to decode information contained in the resulting two-dimensional image, such as 1D linear codes, 2D stacked/matrix codes, OCR fonts, and postal codes. The image captured by the machine vision system may also be subjected to more advanced processing, such as shape recognition or detection algorithms, that provide information about the object of interest in the image.

In robotic sample handling systems, such as blood analyzers and the like, samples are moved to and from diagnostic modules for automatic testing and retesting using a loading rack that holds a plurality of carriers, such as test tubes filled with samples. Proper identification of the samples, decoding of information encoded into labels on the test tube, recognition of the test tube level, and detection of the presence of bubbles may be important for handling and diagnostics. When a target, such as a test tube, contains several labels, processing may become very difficult as images need to be taken from multiple perspectives. Moreover, each image must then be separately processed to decode or reveal the information contained or presented on the test tube.

BRIEF SUMMARY OF THE INVENTION

It is therefore a principal object and advantage of the present invention to provide a system and method for preparing a single panoramic image of a target for autoidentification processing.

It is another object and advantage of the present invention to provide a system and method for more quickly performing image processing of targets that are in motion.

It is a further object and advantage of the present invention to provide a system and method for more quickly performing image processing of targets having information encoded or placed on multiples sides.

It is an additional object and advantage of the present invention to provide a system and method for more quickly processing information about the targets themselves.

In accordance with the foregoing objects and advantages, the present invention provides a system for capturing images of a target, such as a test tube, that is presented in front of an optical imager and rotated 360 degrees. While the target is rotating, the imager of the system captures a series of images which are then stitched together to form a panoramic image of the target. The panoramic image may then be processed to decode any barcode code information placed on the target, capture other information placed on the target, or obtain information about the target or the contents thereof.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
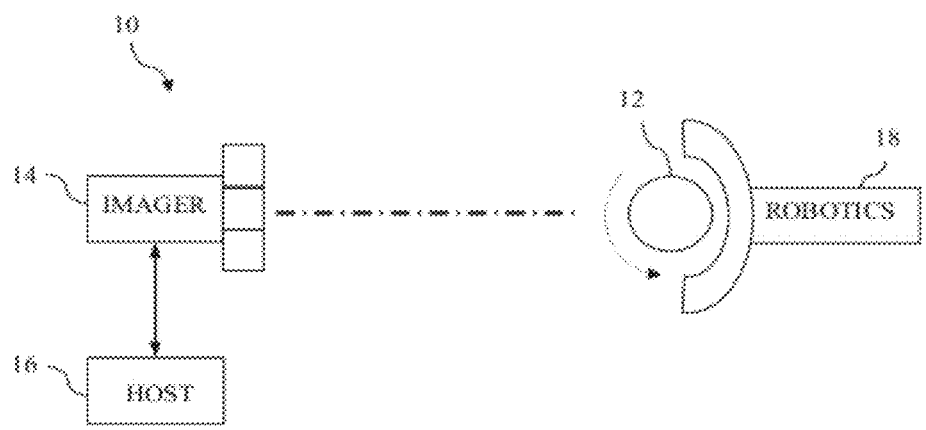
FIG. 1 is a schematic of a system according to the present invention.

Referring now to the drawings, wherein like reference numerals refer to like parts throughout, there is seen in FIG. 1 a storage retrieval system 10, such as an in vitro patient diagnostic test tube system, that is responsible for handling a plurality of targets, referred herein more specifically as patient sample test tubes 12. Tubes 12 are referred to herein can be any form of vessel, such as beakers, bottles, vials, etc., and may contain any variety of fluids (blood, urine, saliva, etc.) for robotic processeding by system 10. In particular, tubes 12 are presented to an optical imager 14, such as a camera, and then rotated by a conventional robotic handler 18 for imaging by imager 14.

Figure 2:
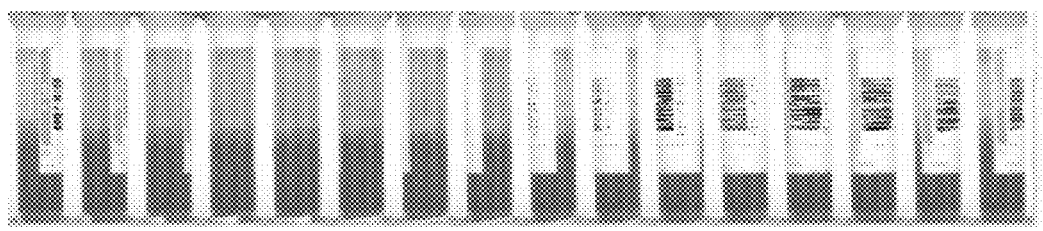
FIG. 2 is a series of images formed into a panoramic image according to the present invention.

Imager 14 is preferably interconnected to a host 16, which can send commands to and receive data from imager 14. As will be described herein, imager 14 will captures multiple images as tube 12 is rotated by handler 18. System 10 may programmed to collect the information encoded on or contained in tube 12, such as by stitching multiple captured images into a single panoramic image of tube 12, reading one or more barcodes posted on tube 12, measuring the liquid level inside tube 12, and determining the thickness of any bubbles on top of the liquid in tube 12. Those of skill in the art will recognize that the present invention is not necessarily limited to test tube handling systems 10 and may be applicable to any system As seen in FIG. 2, a series of images of tube 12 may be captured as tube 12 is rotated through 360 degrees by handler and then stitched according to the present invention to provide a single image for decoding and interpretation. The creation of a single panoramic image is particularly useful for decoding any large 2D barcode labels wrapped around tube 12 or obtaining other information placed on the tubes, such as handwriting, series number, physician name, etc.

Figure 3:
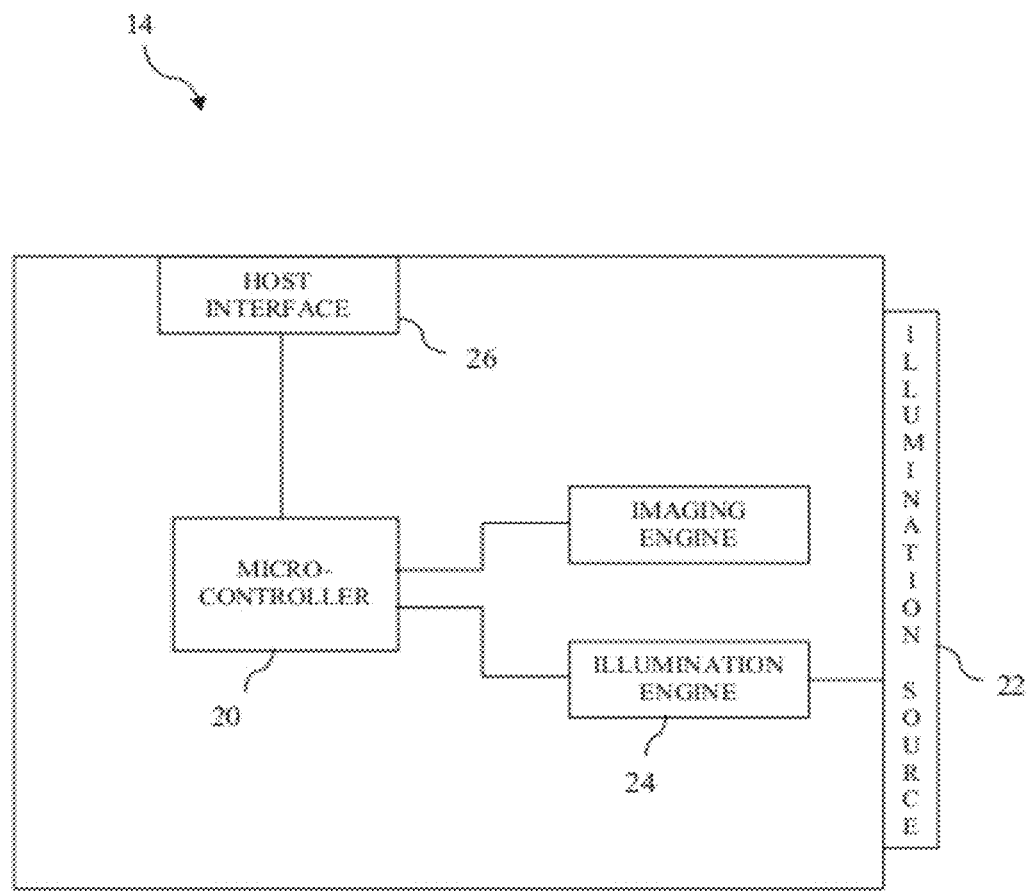
FIG. 3 is a schematic of an imager according to the present invention.

As seen in FIG. 3, imager 14 preferably comprises an illumination source 22, such as one or more LEDs, associated with imager 14 and positioned to illuminate a target positioned in front of imager 14. Imager 14 may comprise various off-the-shelf optical imagers. For example, Honeywell Scanning and Mobility of Skaneateles Falls, N.Y. offers 5080 and 5180 series imagers that are capable of scanning and decoding most standard barcodes including linear, stacked linear, matrix, OCR, and postal codes. Other optical imaging platforms may include the EV12, EV15, EA15, and XA21 imagers available from Intermec Technologies Corporation of Everett, Wash., or any custom imaging packaging sold commercially for incorporation into machine vision or optical imaging systems. It should be recognized by those of skill in the art that the particular model or make optical imaging platforms that may be interfaced with the present invention are not important, provided that the optical imaging platforms include command capabilities through a defined protocol.

System 10 further includes a microcontroller 20 associated with imager 14 for performing digital signal processing. Microcontroller 20 should, at the very least, comprise a conventional programmable microprocessor having on-chip peripherals, such as central processing unit, Flash EEPROM, RAM, asynchronous serial communications interface modules, serial peripheral interfaces, Inter-IC Buses, timer modules, pulse modulators with fault protection modules, pulse width modulators, analog-to-digital converters, and digital-to-analog converters. Additionally, the inclusion of a PLL circuit allows power consumption and performance to be adjusted to suit operational requirements. In addition to the I/O ports, dedicated I/O port bits may be provided. Microcontroller 20 may further include an on-chip bandgap based voltage regulator that generates an internal digital supply voltage from an external supply range. For example, microcontroller 20 may comprise a member of the Blackfin family of processors available from Analog Devices, Inc. of Norwood, Mass., such as the ADSP-BF527 high performance 16/32-bit Blackfin embedded processor core with the flexible cache architecture, the enhanced DMA subsystem, and dynamic power management (DPM). Alternatively, any onboard microcontroller provided as part of imager 14 may be acceptable.

It should be recognized by those of skill in the art that illumination source 22 and microcontroller 20 may be provided integrally with imager 14 or as separate components associated therewith. For example, imager 14 may be provided with an illumination engine 24 for driving an integral or detached illumination source 18 and a host interface 26 for interconnecting to a host 16.

Preferably, imager 14 is programmed to report the decoded barcode data, liquid level and stitched panoramic tube image in a compressed form (such as JPEG) to host 16 through host interface 24 using a conventional protocol, such TCP/IP, through an Ethernet connection, so that system 10 proceeds to present the next tube 12 of interest to imager 14. Interface 24 may also comprise a conventional RS232 transceiver and associated 12 pin RJ style jack or other conventional buses, such as USB, IEEE 1394, I2C, SPI, or PCMCIA, or other connector styles, such as an FFC style. Due to the high volume of tubes 12 normally associated with system 10, and the fact that each tube 12 must be processed individually, vision processing is preferably accomplished by host 16 to meet time requirements. However, those of ordinary skill in the art will recognize that microcontroller 20 could be programmed with logic for performing all necessary image decoding and interpretation if fast processors are provided or if processing time is not critical.

Imager 14 is preferably configured as a slave device, accepting control and configuration commands from and returning the information to host 16. After machine vision tasks are finished, imager 14 may report the analytic results and the compressed stitched image to host 16. An exemplary machine vision process 30 may be seen in FIG. 4. More particularly, a series of images are first captured 32 as tube 14 is rotated 360 degrees. Image stitching 34 is then performed using stitching coefficients previously determined during off-line calibration 36. The stitched image may then be processed for barcode decoding 38, liquid level detection 40, and/or image compression 42, and the results of any of these steps are assembled and reported 44 to host 16.

As illustrated in FIG. 2, a series of the tube images are stitched together first, and then the barcode decoding 38 and liquid level detection 40 are performed on the stitched image. However, as further seen in FIG. 4, the liquid level detection is performed after the barcode is decoded as the liquid level detection must usually be performed in a region of interest (ROI) where the liquid level is visible. The information where the barcode is located obtained in the conventional barcode decoding process will aid in finding the liquid level region of interest. Off-line calibration 36 is used to get a rough estimation of the image perspective alignment coefficients, which greatly relieve the computation burden of on-line image stitching 34.

The step of image stitching 34 involves combining multiple photographic images with overlapping fields of view to produce a segmented panorama or high-resolution image. Commonly performed through the use of computer software, most approaches to image stitching require nearly exact overlaps between images and identical exposures to produce seamless results. This process is also known as mosaicing. Stitching process 34 involves three stages: image calibration, image registration, and image blending. Image calibration consists of processing to improve image quality and ease of stitching, such as perspective correction, vignetting correction, and chromatic aberration correction. Image registration involves analysis for translation, rotation, and focal length. Alternatively, direct or feature-based image alignment methods may be used. Direct alignment methods search for image orientations that minimize the sum of absolute differences between overlapping pixels. Feature-based methods determine proper image orientations by identifying features that appear in multiple images and overlapping them. Finally, image blending involves combining of the images and may further entail color correction to match the adjoining areas of the component images for color, contrast, and brightness to avoid visibility of the seams, dynamic range extension, and motion compensation, such as deghosting and deblurring, to compensate for moving objects.

Generally, image stitching is a very computation-intensive process, and usually not suitable to be performed on-line on imagers 14 which are often limited by both speed and memory. However, by shifting some of the computation to off-line calibration 36, operational image stitching computations can be greatly improved. Off-line calibration 36 is grounded in the fact that imager 14 is fixed mounted, so the relative position between the placement of tubes 12 and imager 14 is fixed. Thus, the perspective transformation from the imager of tube 12 to imager 14 is almost fixed. Because the sample tube is held still upright by robotic handler 18, see FIG. 2, the geometrical perspective shift parameters from one image to the next will be limited to the horizontal direction. The variation for the other geometrical parameters, such as vertical direction translation shift, scale, and rotation shift are small or negligible, thereby greatly simplifying the image registration process by limiting the search space. If tube rotation speeds are kept constant by robotic handler 18, the time difference between subsequent image captures should be relatively constant. The optimal adjustment between imager capture speed and image rotation speed can provide a nearly exact overlap between the consecutive tube images and the shift parameters should be nearly identical during the stitching process. In system 10, imager 14 may also be configured to use identical exposures when capturing images to produce more seamless results. Finally, as the stitched images are used mainly for barcode decoding and liquid level detection, not for viewing, a small boundary effect may be tolerated. Therefore, stitching can be further simplified, such as by avoiding the blending, color correction, chromatic correction required for images that are to be viewed visually. Based on these characteristics of system 10, most of the image stitching computations, i.e., the initial estimation of image stitching geometry shift parameters, may be transferred to off-line processing and be pre-computed by host 16.

Following is an example stitching process 34, although those of ordinary skill in the art will recognize that other methods may be used in connection with system 10. Let x'=[x',y',1] and x=[x,y,1] denote the corresponding position between the current image and previous image. The most general planar 2D transform is the eight-parameter perspective transform like $$x' = Hx = \begin{bmatrix} h_{00} & h_{01} & h_{02} \\ h_{10} & h_{11} & h_{12} \\ h_{20} & h_{21} & h_{22} \end{bmatrix} x \; x' = \frac{h_{00}x + h_{01}y + h_{02}}{h_{20}x + h_{21}y + h_{22}}, \quad (1)$$

$$y' = \frac{h_{10}x + h_{11}y + h_{12}}{h_{20}x + h_{21}y + h_{22}}$$

The image registration is just seeking to estimate H using the corresponding matching image points from the consecutive two images. During off-line processing, it is possible to use a calibration image to get an estimated transform $\overline{H}$. The real transform should be $$x'=Hx=(\overline{H}+\Delta H)x=\overline{H}x+\Delta Hx \quad (2)$$

Reviewing the characteristics of system 10 described above, ΔH should be very small. As noted above, a search for ΔH can be limited to the horizontal direction, i.e., $\Delta h_{02}$ within a lot of pixels. One of such example is shown in FIG. 3, where $\Delta h_{02}$ is only searched within a few pixels. In system 10, the off-line estimation of the transform matrix $\overline{H}$ is estimated from PC and saved in the camera non-volatile memory. Another important factor of process 34 is that with the default $\overline{H}$ is a necessity for some two tubes images where there are not very strong salient local structure (such as corners, text, lines, etc) among the images (like sub-images 3 to 5 from the left in FIG. 2) and the stitching is error-prone or impossible, we can use default H to replace H directly in this case. Those of skill in the art will recognize that, during calibration, more than transformation matrix should be calculated and used later. For example, camera calibration (intrinsic parameters estimations) is well known, and it can be used to convert the world coordinates to the image coordinates. With the present invention, imager 14 is fixed and tube 12 should be held upright vertical. As a result, only the scalars converting the number of pixels to millimeters is needed and easy to do in the calibration process.

To further reduce the computation for stitching process 34, the requirement for tube stitching reconstruction fidelity may be changed from the preferred stitching process 34. As explained above, the tube rotation images are stitched mainly for the purpose of reading the barcode and measuring liquid level. As long as the barcode reading and liquid level detection are right, some distortion and boundary effects are tolerated. Thus, the estimation of the perspective transform (both off-line and on-line) may be limited to a few of the eight parameters.

Figure 4:
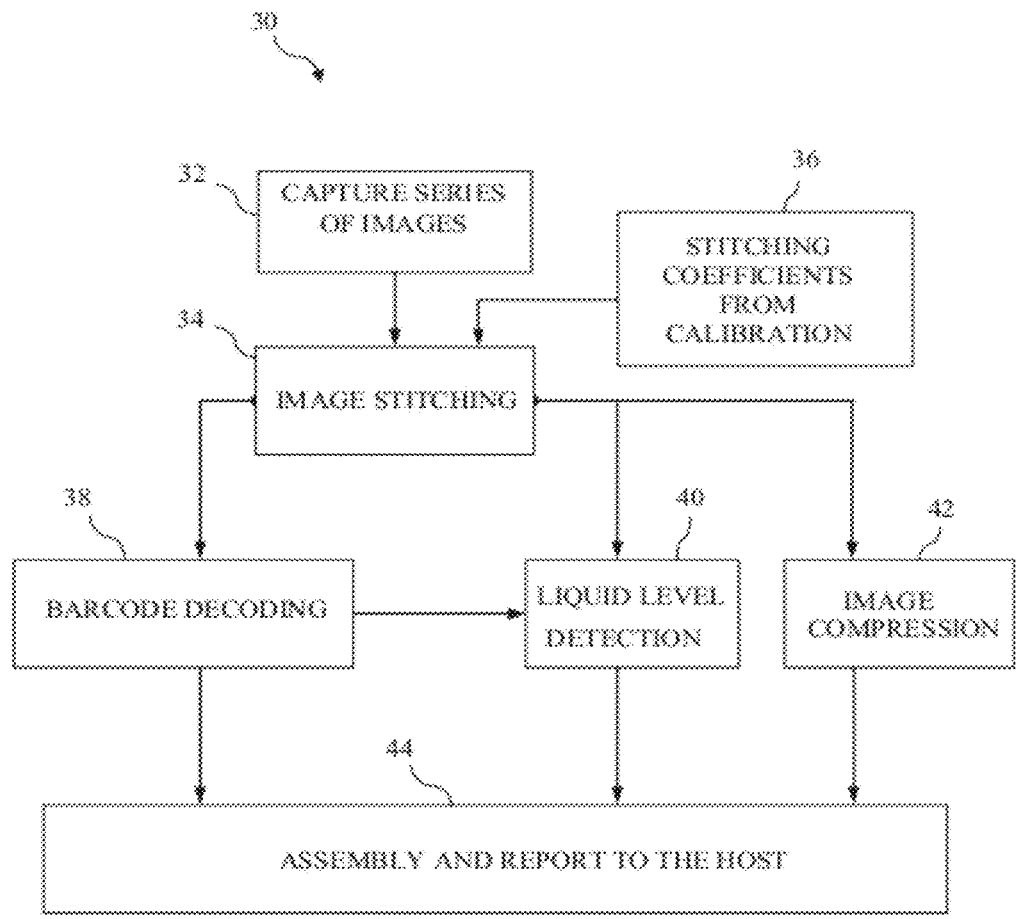
FIG. 4 is flowchart of an image stitching and interpretation process according to the present invention.
Figures 5A, 5B, 5C, 5D, 5E, 5F, 5G, 5H, 5I, 5J, 5K, 5L, 5M:
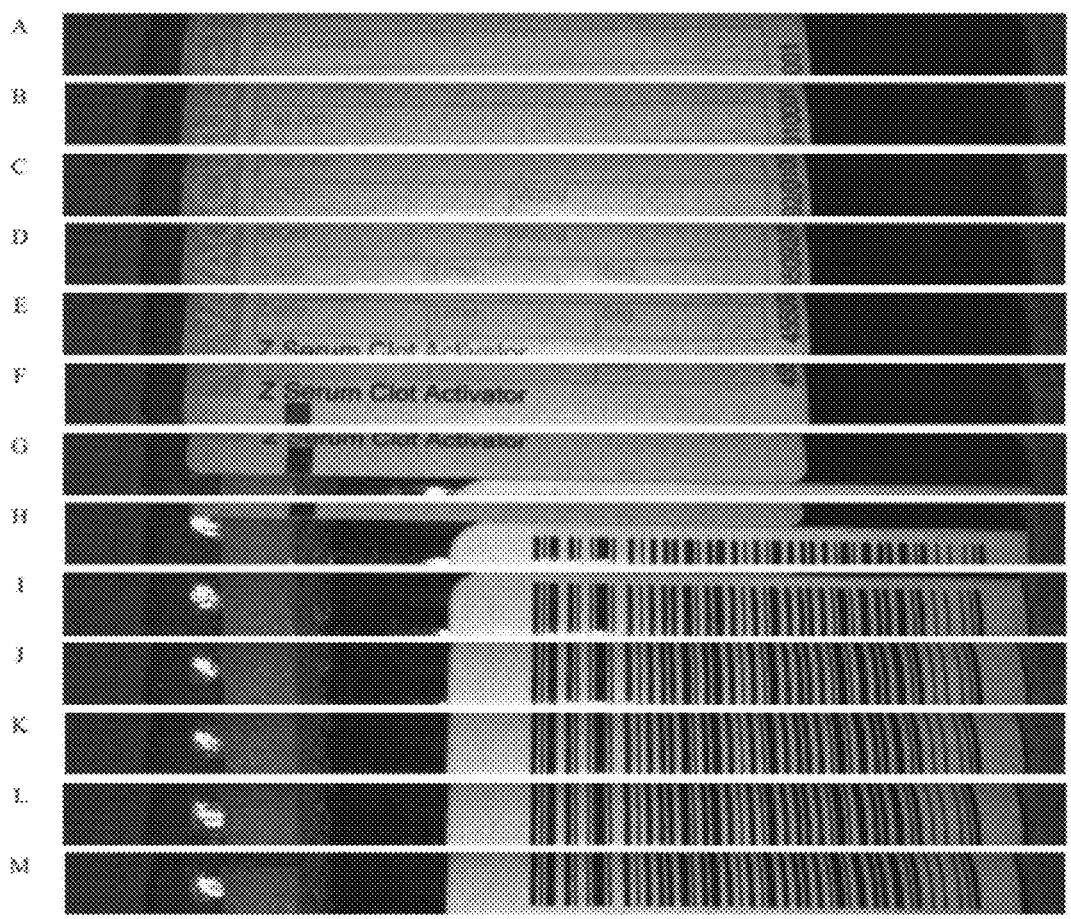
FIG. 5 is a series of images to be formed into a panoramic image according to the present invention.
Figures 5N, 5O, 5P, 5Q, 5R, 5S, 5T:

FIG. 5 shows an example of stitching process 34, where FIGS. 5A through 5S give the tube rotation image according to the time line, and FIG. 5T gives the stitched tube image result. In FIG. 4, the off-line and on-line estimation of the perspective transform coefficients are limited only to the vertical translation shift. Doing so makes the stitched image especially fast. However, as seen in FIG. 5T, there are some clear boundary effects on the stitched result in FIG. 5T. The barcode in the FIG. 5T is one-dimensional and, although the stitched image appears somewhat poor, it is sufficient for reading 1-D barcodes due to the redundancy built in the 1-D barcode symbology. However, in some cases, the parameters search must be expanded to all of the coefficients in order to read 2-D barcodes where the dimensions of the 2-D barcodes are larger than the overlap dimension between each tube rotation subimage, or where other important information, such as handwriting on the tube label, must be recorded.

Figures 6A, 6B, 6C, 6D:
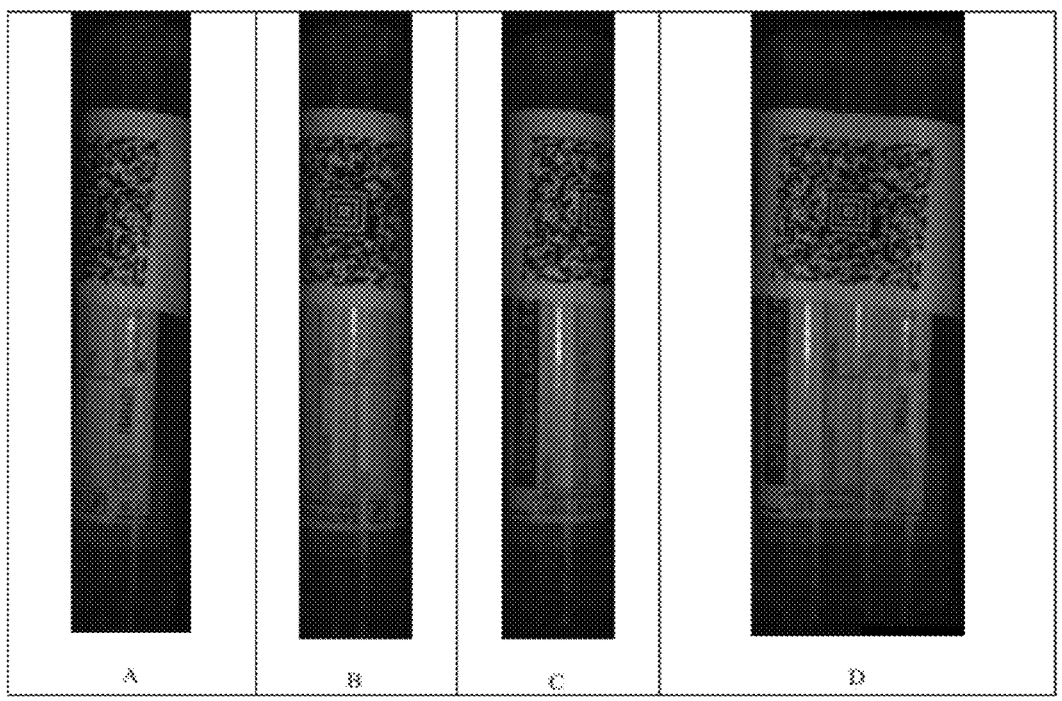
FIG. 6 is a series of images formed into a panoramic image according to the present invention.

FIG. 6 shows such an example where subimages of FIGS. 6A through 6C are three consecutive tube rotation images and FIG. 6D gives the stitched tube result. None of tube rotation images in FIGS. 6A through 6C alone contain the whole 2D matrix Aztec codes, therefore, the 2D matrix Aztec can only be read on the entire stitched image. As the readability of 2D barcode relies greatly on image quality, a boundary effect like that of the 1-D barcode shown in FIG. 5 is not tolerable, and all the eight coefficients of perspective transform have been estimated.

With respect to barcode decoding 38, conventional imagers 14 may be equipped with algorithms for decoding all the symbologies shown in Table 1. Host 16 may therefore determine which symbologies are enabled and disabled for decoding.

TABLE 1

| | | |
|---|---|---|
| Codabar | EAN/JAN-13 | PDF417 |
| Code 39 | EAN/JAN-8 | Micro PDF417 |
| I 2 of 5 | RSS-14 | DataMatrix |
| Code 93 | RSS-Limited | MaxiCode |
| Code 128 | RSS-Expanded | Aztec Code |
| UPC-A | PosiCode | |
| UPC-E0 | Code 49 | |

Barcode symbologies and their decoding algorithms follow the international barcode standards and those of skill in the art will instantly appreciate how to accomplish this functionality through the use of off-the-shelf imagers 14 or decoding packages. As described below, barcode location information may be used for liquid level detection 40 to narrow down the searching area or locate the region of interest.

Liquid level detection 40 involves measuring roughly how much liquid is located within tube 12 and checking the thickness of any bubble on top of the liquid in tube 12. The first step in liquid level detection 40 involves locating the region of interest (ROI) where liquid level detection is desired. Typically, a barcode label is posted on a tube 12, such as that seen in FIG. 2, so that there is a clear window on the reverse side of tube 12 between the two edges of the label that provides a clear view of liquid inside the tube. Sometimes, however, the barcode label may be posted between other labels, such as in FIG. 5(20), such as when is a second label with handwriting or information other than the barcode. The liquid level can therefore only be measured from parts of tube 12 not covered by the labels.

Figure 7A:
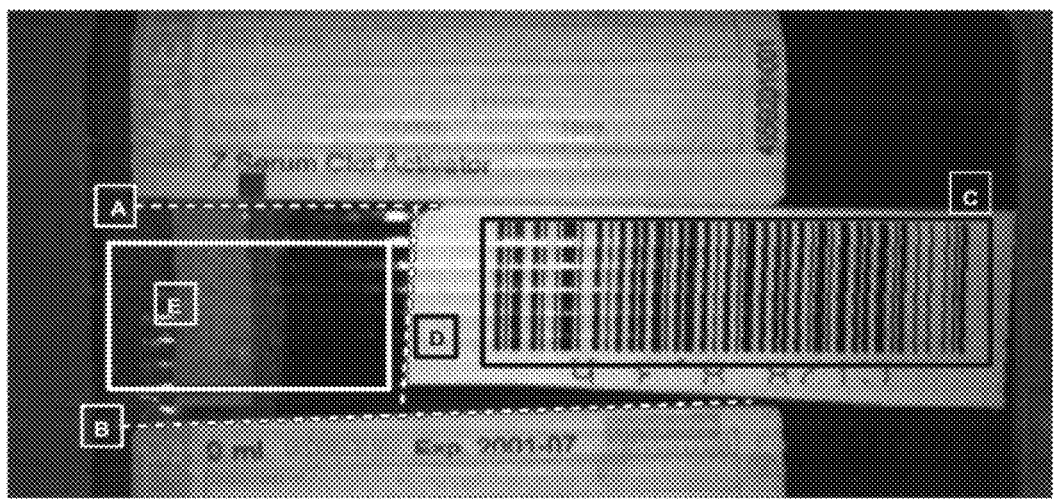
FIG. 7 is a series of images illustrating a barcode decoding and fluid level detection process according to the present invention.

The first step in liquid level detection 40 therefore involves the determining the two strongest horizontal label edges A and B starting from the leftmost of the images as seen in FIG. 7A. From any previous barcode decoding, the bounding window of the barcode should be known, shown by window C in FIG. 7A. With the location of lines A and B and window C, we can accurately determine if there are one label or two labels. For example, if the barcode bounding box is not located between the lines A and B of FIG. 7A, there is only one label and the water level region of interest can be determined from the location of lines A and B. Otherwise, there are two labels, such as seen FIG. 7A, and left barcode label boundary line D must be determined to identify the liquid level region bounded by lines A, B and D. Window E in FIG. 7A shows such an example of the region of interest on a tube 12 having multiple labels.

Figure 7B:
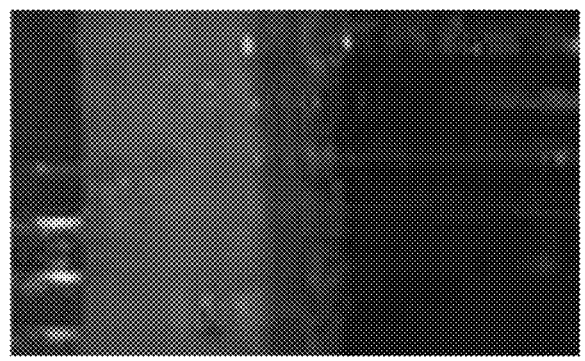
Figure 7C:
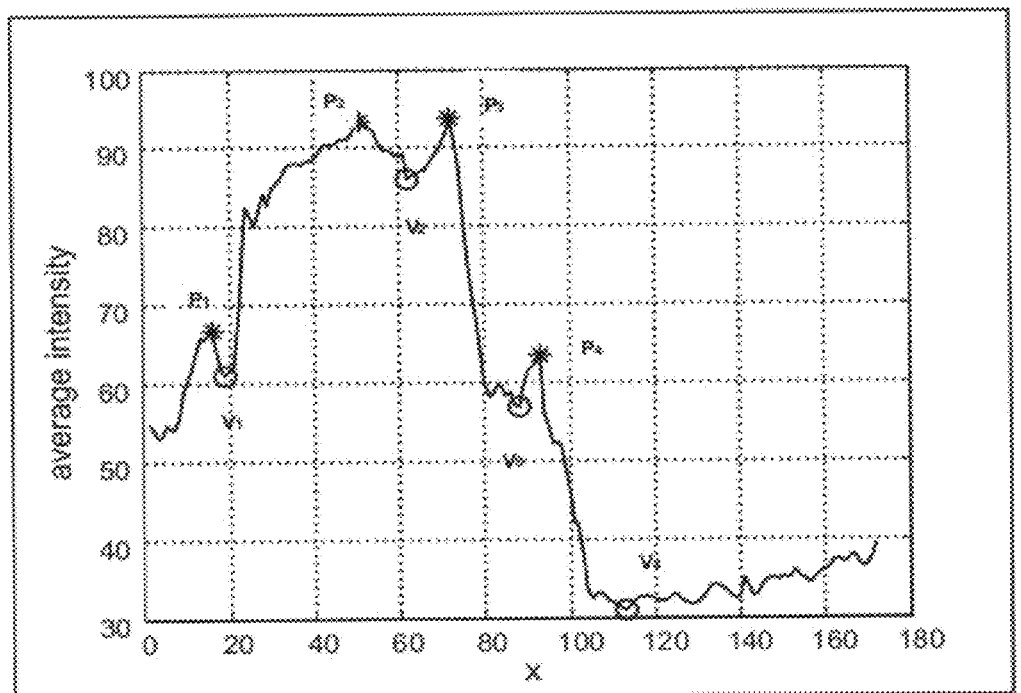

The next step in liquid level detection 40 is to extract the region of interest (window E of FIG. 7A) from the full image, as seen in FIG. 7B. Next, the liquid level may be deducted by extracting the horizontal profile of the liquid level region of interest by computing the mean values of the extracted region of interest rows, as seen in the profile of FIG. 7C. The local maxima of the profile (peaks, $P_1, P_2, \ldots, P_M$) and local minima of the profiles (valleys, $V_1, V_2, \ldots, V_M$) are then determined. The place where any bubble starts and ends can also be deducted from these peaks and valleys.

The neighboring peak-to-valley difference $E_{i1}=P_i-V_i$, $i=1, 2, \ldots, M$ is first computed and sorted. Then, up to two of the biggest $E_s$ and $E_e$, $s<e$, $s, e \in [1,M]$, which are greater than a preset threshold T, are removed and the liquid level L and bubble thickness L an be determined by the following formula, which makes the liquid level detection robust to the image noises and some unwanted specular small artifacts, or liquid residue on the tubes $$\begin{cases} L = \frac{(P_e + V_e)}{2}, B = \frac{(P_e + V_e)}{2} - \frac{(P_s + V_s)}{2}, & E_s > T, E_e > T \\ L = \frac{(P_s + V_s)}{2}, B = 0, & E_s > T, E_e < T \end{cases} \quad (3)$$

Figure 7D:
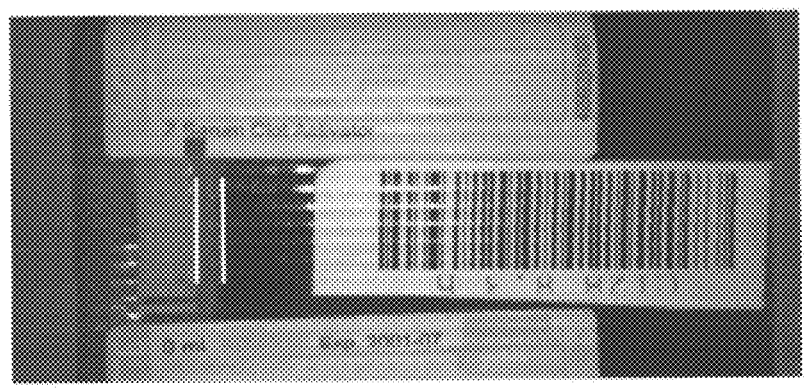

The detection result is shown in FIG. 7D. The scalar conversion discussed above with respect to calibration may be used to convert the thickness of the serum bubble into millimeters or to indicate relative size, such as small, medium or large.

It should be recognized by those of skill in the art that the panoramic image may be used for other purposes, such as determining the type of test tube or other vessel, or identifying the presence of a cover or cap on the vessel. For example, application Ser. No. 12/145,619, hereby incorporated by reference in its entirety, details a system and method for determining the presence of a cap on a test tube as well as identifying the type of test tube and cap, using images captured by an optical imager.

What is claimed is:

1. A machine vision apparatus, comprising:
   a robotic handler adapted to rotate an object comprising a test tube;
   an imager positioned to capture a plurality of images of said test tube as said test tube is being rotated by said handler;
   a microcontroller associated with said imager, wherein said microcontroller is programmed to form a single panoramic image of said object from said plurality of images and then extract information about said test tube from said single panoramic image comprising the level of liquid in said test tube.

2. The apparatus of claim 1, wherein said information extracted from said single panoramic image further comprises encoded data.

3. The apparatus of claim 1, wherein said information extracted from said single panoramic image further comprises barcode information encoded into a barcode label and placed on said test tube.

4. The apparatus of claim 1, wherein said information extracted from said single panoramic image further comprises the thickness of any bubble on top of the liquid in said test tube.

5. The apparatus of claim 1, wherein said microcontroller is further programmed to transmit said decoded information to a remotely positioned host.

6. The apparatus of claim 5, wherein said microcontroller is further programmed to identify characteristics of said object and transmit said characteristics to said host.

7. The apparatus of claim 1, wherein said microcontroller is further programmed to transmit said single panoramic image to said remotely positioned host.

8. The apparatus of claim 7, wherein said microcontroller is further programmed to compress said single panoramic image prior to transmittal to said host.

9. The apparatus of claim 1, wherein said microcontroller is programmed create a single panoramic image of said object by calibrating said plurality of images according to a predetermined calibration factor, registering said plurality of images to substantially align the edges of said plurality of images, and blending said plurality of images to form said single panoramic image.

10. A method of extracting information from a test tube, comprising the steps of:
    rotating said test tube using a robotic handler in front of an optical imager;
    capturing a plurality of images of said object using said imager as said object is rotated by said robotic handler;
    processing said plurality of images to form a single panoramic image of said test tube;
    interpreting said single panoramic image to extract information from said single panoramic image, wherein said information comprises the level of liquid in said test tube; and
    transmitting said extracted information to a remotely positioned host.

11. The method of claim 10, wherein said extracted information further comprises information encoded into a barcode positioned on said object.

12. The method of claim 10, wherein said extracted information further comprises information about any contents of the object.

13. The method of claim 10, wherein said extracted information further comprises handwriting placed on the object.

* * * * *